United States Patent [19]

Borodic

[11] Patent Number: 5,401,243
[45] Date of Patent: * Mar. 28, 1995

[54] CONTROLLED ADMINISTRATION OF CHEMODENERVATING PHARMACEUTICALS

[75] Inventor: Gary E. Borodic, Canton, Mass.

[73] Assignee: Associated Synapse Biologics, Boston, Mass.

[*] Notice: The portion of the term of this patent subsequent to Feb. 2, 2010 has been disclaimed.

[21] Appl. No.: 46,097

[22] Filed: Apr. 12, 1993

Related U.S. Application Data

[63] Continuation-in-part of Ser. No. 4,090, Jan. 13, 1993, Pat. No. 5,298,019, which is a continuation of Ser. No. 570,395, Aug. 21, 1991, Pat. No. 5,183,462.

[51] Int. Cl.$^6$ .......................................... A61M 31/00
[52] U.S. Cl. ..................................... 604/51; 128/898
[58] Field of Search ................................ 604/49–53, 604/28; 128/749, 898, 632, 635, 774, 782, 741, DIG. 13

[56] References Cited

U.S. PATENT DOCUMENTS

| | | | |
|---|---|---|---|
| 2,979,055 | 4/1961 | de Beer et al. | 128/214 |
| 3,898,983 | 8/1975 | Elam | 128/2 |
| 4,331,145 | 5/1982 | Winter | 128/207.21 |
| 4,445,515 | 5/1984 | DiResta | 128/632 |
| 4,501,582 | 2/1985 | Schulz | 604/52 |
| 4,522,302 | 6/1985 | Paikoff | 206/570 |
| 4,664,911 | 5/1987 | Uhr et al. | 424/85 |
| 4,810,243 | 3/1989 | Howson | 604/31 |
| 4,880,014 | 11/1989 | Zarowitz et al. | 128/734 |
| 4,932,936 | 6/1990 | Dykstra et al. | 604/51 |
| 5,053,005 | 10/1991 | Borodic | 604/51 |
| 5,097,834 | 3/1992 | Skrabal | 128/632 |

OTHER PUBLICATIONS

Blitzer, "Botulinum Toxin Injection For The Treatment Of Oromandibular Dystonia", *Presented at Meeting of the American Laryngological Association*, (1988).
Borodic, "Botulinum A Toxin For The Treatment Of Spasmodic Torticollis: Dysphagia And Regional Toxin Spread", *Head & Neck*, (1990).
Borodic, "Dose–Response Relationships In Patients Treated With Botulinum Toxin For More Than Three Years", *Ear, Nose and Throat*, 67:914 (1988).
Borodic, "Blepharospasm And Its Treatment, With Emphasis On The Use Of Botulinum Toxin", *Plastic and Reconstructive Surgery*, (1989).
Borodic, "Innervation Zone Of Orbicularis Oculi Muscle And Implications For Botulinum A Toxin Therapy", *Ophthalmic Plastic and Reconstructive Surgery*, 7(1):54–60 (1991).
Das, "Effect of Treatment With Botulinum Toxin On Spasticity", *Postgraduate Medical*, 65:208–210 (1989).
Das, "Botulinum Toxin In Treating Spasticity", *BJCP*, 43:401–403.
Dunlop, "Neuroscience Applied To Clinical Problems Botulinum–A Toxin Used For Chemodenervation Of Muscles In Spasm", (Abstract).
Evans, "Botulinum Neurotoxin Type B Its Purification, Radioiodination And Interaction With Rat–Brain Synaptosomal Membranes", *Eur. J. Biochem.*, 154:409–416 (1986).
Gelb, "Controlled Trail Of Botulinum Toxin Injections In The Treatment Of Spasmodic Torticollis", *Neurology*, 39:80–84 (1989).
Gluckstein, "Clinical Use Of Botulinum Toxin", *Current Bibliographies In Medicine*, Jan. 1987–Sep. 1990.

(List continued on next page.)

*Primary Examiner*—Sebastiano Passaniti
*Attorney, Agent, or Firm*—Testa, Hurwitz & Thibeault

[57] ABSTRACT

The activity of chemodenervating agents can be ascertained by injecting locally a known quantity of the agent and determining the extent of inhibition of acetylcholine release about the locus resulting therefrom. Inhibition of acetylcholine release is indicative of denervation in a muscle, therefore the extent of inhibition of acetylcholine release is coextensive with the zone of denervation induced by the quantity of the agent.

16 Claims, 2 Drawing Sheets

OTHER PUBLICATIONS

Gonnering, "Negative Antibody Response To Long-Term Treatment Of Facial Spasm With Botulinum Toxin", *American J of Ophthalmology*, 105:313–315 (1988).

Jankovic, "Botulinum A Toxin For Cranial-Cervical Dystonia: A Double-Blind, Placebo-Controlled Study", *Neurology*, 37:616–623 (1987).

Ludlow, "Spasmodic Dysphonia: Botulinum Toxin Injection After Recurrent Nerve Surgery", *Otolaryngol Head Neck Surg*, 102:122–131 (1990).

Singh, "Molecular Topography And Secondary Structure Comparisons Of Botulinum Neurotoxin Types A, B And E", *Molecular and Cellular Biochemmistry*, 86:87–95 (1989).

Snow, "Treatment Of Spasticity With Botulinum Toxin: A Double-Blind Study", *Annals Of Neurology*, 28:512–515 (1990).

Tsui, "Production Of Circulating Antibodies To Botulinum-A Toxin In Patients Receiving Repeated Injections For Dystonia", (Abstract).

Tsui, "A Pilot Study On The Use of Botulinum Toxin In Spasmodic Torticollis", *Can. J. of Neurological Sciences*, 12:314–316 (1985).

Tsui, "Local Treatment Of Spasmodic Torticolli With Botulinum Toxin", *Can. J. Neurol. Sci.*, 14:533–535 (1987).

VanZandijcke, "Treatment Of Bruxism With Botulinum Toxin Injections", *J. Neurol., Neurosurg., Psychiatry*, 53:530 (1990).

Patrinely, "Essential Blepharospasm: A Reivew", *Reproduced From Geriatric Ophthalmology*, 27–31 (Jul.-/Aug. 1986).

Engstrom, et al., "Effectiveness of Botulinum Toxin Therapy For Essential Blepharospasm", *Ophthalmology*, 94:971–975 (1987) (Abstract).

Jankovic, "Botulinum A Toxin in the Treatment of Belpharospasm", *Advanced in Neurology*, 49:467–472 (1988).

Davidorf, "Treatment of Strabismus with Botulinum", *Contemporary Ophthalmic Forum*, 5:(6) Nov./Dec. 1987).

Magoon, "The Use of Botulinum Toxin Injection as an Alternative to Strabismus Surgery", *Contemporary Ophthalmic Forum*, 5:222–229 Nov./Dec. (1987) (Abstract).

Biglan, et al., "Experience with Botulinum A Toxin (Oculinum) in the Treatment of Strabismus", *Contemporary Ophthalmic Forum*, 5:230–240 (Nov./Dec. (1987).

Duchen, "Changes in Motor Innervation and Cholinesterase Localization Induced by Botulinum Toxin in Skeletal Muscle of the Mouse: Differences Between Fast and Slow Muscles", *J. Neurology Neurosurgery and Psychiatry*, 33:40–54 (1970).

Duchen, "Histological Differences Between Soleus and Gastrocnemius Muscles in the Mouse After the Local Injection of Botulinum Toxin", (Abstract).

CONTROLLED ADMINISTRATION OF CHEMODENERVATING PHARMACEUTICALS

RELATED APPLICATIONS

This application is a continuation-in-part of application Ser. No. 08/004,090, now U.S. Pat. No. 5,298,019, by G. E. Borodic, filed Jan. 13, 1993, which is a continuation of Ser. No. 07/570,395, by G. E. Borodic, filed Aug. 21, 1990, now U.S. Pat. No. 5,183,462; the entire disclosures of which are incorporated herein by reference.

BACKGROUND OF THE INVENTION

This invention relates to controlled administration of chemodenervating agents, e.g., botulinum toxin-derived pharmaceuticals, useful in attenuating neural stimulation and spasmotdic activity of muscle. More particularly, the invention relates to a method of standardizing denervating pharmaceuticals and novel dosage forms based thereon which permit medically safe administration in the management of a variety of disease states and injuries characterized by involuntary muscle spasm or hyperactivation. The invention also relates to novel methods of administering chemodenervating agents in a controlled and reproducible manner so as to confine their effect to a given region of muscle mass while minimizing paresis in adjacent muscle tissue. The invention further relates to testing the duration of action and diffusion potential of a new formulations of botulinum toxin-based therapeutic agents.

Pharmaceutical grade preparations from the toxin produced by Clostridium botulinum have been available for many years from Dr. Allan Scott and the Kettlewell Ophthamology Institute of San Francisco, Calif., and now are sold commercially by Allergan Pharmaceuticals, Inc. Many other materials toxic to neuromuscular transmission are known, such as tetanus toxin and various subtypes of botulinum toxin. Botulinum toxin preparations recently have been approved for the treatment of blepharospasm and strabismus, and clinical trials are underway on the treatment of spasmodic torticollis. Dykstra et al have proposed in U.S. Pat. No. 4,932,936 that botulinum toxin can be used in the treatment of spasmodic sphincter muscle which leads to urinary incontinence ("neurogenic bladder") characteristic of some forms of cancer. A survey of the literature provides evidence for the potential use of chemodenervating agents such as botulinum toxin in the treatment of other significant spasmodic diseases including jaw dystonias, occupational dystonias, corneal ulceration (protective ptosis), spasmodic dysphonia, and various forms of facial dyskinesis including Meige syndrome, hemifacial spasm, aberrant regeneration of facial nerves, and apraxia of eyelid opening.

Treatment of these diseases involves injection of a chemodenervating agent, currently a botulinum preparation, directly into the muscle, using, for example, a fine gauge teflon-coated needle under electromyographic control to aid the physician in locating the intended intramuscular locus of the injection. The pure active toxin is believed to be the single most toxic material know. A sufficient dose of the toxin acts on striated muscle to block release of the acetylcholine neurotransmitter from the presynaptic membrane resulting in varying degrees of effective denervation of the muscle in regions contacted by the toxin. This results in an increase in post-synaptic acetylcholinesterase activity and an increase in the population of acetylcholine receptors, effects which occur as a characteristic physiological response to denervation. After a period of days, the axon terminals develop sprouting, and over a period of several months, collateral motor axons establish new neuromuscular connections with the muscle fiber. As neuromuscular connections are regenerated, full function of the muscle returns along with the spasmodic contractions or hyperstimulation symptomatic of the disease. A drawback to this therapy is the equirement for indefinite repeated injections. The animal ptosis model described herein permits the duraton of action of various botulinum toxin preparations, formulations or immunotypes to be determined, sothat greater therapeutic benefit can be derived from botulinum toxin treatment.

With the exception of the emerging spasmodic torticollis therapy, development of the therapeutic uses of botulinum toxin preparations has been limited to small muscles which may be treated with lower doses and have limited risk of toxin spread. Development of the therapies has proceeded empirically using low doses without theoretical basis or clinical data predictive of the distribution of the toxin in vivo. Currently, toxin preparations are quantified by measuring the $LD_{50}$ in white mice. $LD_{50}$ in white mouse equals one international unit or I.U.

The treatment of blepharospasm with botulinum toxin as disclosed by Borodic et al in Plastic and Reconstructive Surgery, (March, 1989) is illustrative of a clinical protocol for use of the toxin. Generally, for bilateral blepharospasm, a starting dose totalling 10 to 20 IU is injected at 4 to 6 sites in the upper and lower eyelid of each eye spaced laterally from the midline of the lid and close to the lash base of the upper lid. Injections above the brow are given only if significant involuntary movements are recurring in this region. If the toxin is injected too close to the upper lid fold, diffusion through the orbital septum can weaken the levator palpebral superioris muscle and induce ptosis. If the toxin is injected too medially in the lower lid, the naso-lacrimal pumping mechanism can be weakened excessively resulting in epiphora. With an appropriate dose, because the muscle is only partially weakened, enough strength and neural control remain so that a treated muscle still can perform its primary voluntary function. The degree of weakening from denervation can be "titrated" empirically for particular patients by altering the dose.

SUMMARY OF THE INVENTION

This invention provides novel methods of measuring the local, in vivo activity of neurotoxin-derived chemodenervation pharmaceutical preparations, such as botulinum toxin-derived preparations. Exploitation of the method permits manufacture of the preparation in standardized dose forms of predictable clinical effect labeled to indicate the denervation zone or field that will be induced by a unit dose of the preparation when injected at a locus in vivo. Provision of such dosage forms and the teaching disclosed herein permits the physician to preselect appropriate dosage in advance of injection of the preparation and to chemodenervate a given volume of muscle mass while essentially confining diffusive spread of the toxin within that predetermined volume. Thus, practice of the method of the invention permits the physician to avoid or minimize complications in therapies involving such agents, i.e., to avoid inducing unwanted dysphagia or partial paralysis in muscles adjacent the site of injection, which may be directly or indirectly life threatening, incapacitating, or disfiguring. Practice of the invention permits more exacting application of the toxin and facilitates its use in large muscle groups of the limbs and trunk. Another application and practice of the invention involves monitoring the duration of action of experimentally produced botulinum toxin formulations and subtypes.

In one embodiment, the foregoing can be accomplished by determining experimentally within a muscle of an experimental animal the spatial extent of inhibition of acetylcholine release about a site of injection of a unit quantity of the preparation. The determination may be made in several ways. One can determine the extent of inhibition of muscle stimulation in regions spaced apart from the site of injection by electrophysiologic testing, for example, electromyography, such as single fiber electromyography. This method of determining the spatial extent of inhibition of acetylcholine release is most direct but also most cumbersome. More easily conducted indirect measurements currently are preferred. These techniques involve postmortem sectioning of muscle at regions spaced apart from the site of injection and determining the extent of denervation by indirect methods which take advantage of the known physiologic effects of neurotoxin based chemodenervation phenomena. For example, one may employ suitably labeled monoclonal antibody or polyclonal antisera raised against an epitope or epitopes of the toxin preparation which remain exposed or becomes exposed upon binding of the toxin to the motor end plate, against acetylcholine receptors (which increase significantly in response to denervation), or against acetylcholinesterase (which also increases upon denervation). The currently preferred method is to determine the local concentration of acetylcholinesterase in regions of the muscle spaced apart from the site of injection by colorimetric estimation of enzyme activity.

Another method of determining the extent of denervation is by determining the change in diameter of muscle fibers before and after injection of the chemodenervating agent. The variability in muscle fiber diameter can be correlated to the dose of toxin administered, and to the amount of acetylcholinesterase activity. The extent of the denervation field established by a given dose of toxin thus can be determined by measuring the extent of muscle fiber atrophy induced by the toxin at various distances from the point of injection. This method is carried out by administering the desired dose of toxin to the muscle, and allowing it to take effect, e.g., for about two to five weeks. Biopsies of the muscle are taken, and the average diameters of the muscle fibers in the biopsy are ascertained. The biopsies are taken from the treated muscle at various distances from the injection site. The diameters of the muscle fibers are averaged by standard statistical methods to obtain a mean fiber diameter for each biopsy sample. The change in muscle fiber diameter is indicative of the degree of fiber atrophy. Significant atrophy occurs where the toxin has effectively denervated the muscle, causing the muscle fibers to decrease in diameter. Therefore, the size and extent of the denervation field can be established by determining the decrease in muscle fiber diameter occurring at increasing distances from the point of injection. The boundary of the denervation field will be the distance from the injection point (or points) at which little or no reduction in the muscle fiber diameter can be detected.

A method for rapidly approximating the denervating effect of a a given amount of a chemodenervating preparation is also the subject of the present invention. Chemodenervation effects in vivo can be approximated rapidly by interrupting observable reflexive motion in an animal with a chemodenervating preparation. This can be effectively carried out, for example, using an animal ptosis model, in which a known amount of a test preparation is injected into a muscle or muscle group which controls eyelid movement, and the resulting ptosis (eyelid drooping) in the animal is observed. The degree of ptosis can be related to the denervating activity of the preparation. In one embodiment, a quantity of the preparation is injected into the levator palpebral superioris muscle of the animal, i.e., at a point bisecting the line between the animal's eyes or on one side (ipsilaterally). A sufficiently potent preparation will migrate laterally into the muscles responsible for eyelid movement, thereby inducing ptosis in the animal. The degree of ptosis is indicative of the extent of denervation caused by the dose injected. This method has the advantage that the animal need not be sacrificed, and the results can be evaluated within a relatively short time, e.g., about 48 hours. This method allows the clinician to quickly approximate the extent of diffusion of a given dose of toxin and to dispense with removing, sectioning and staining muscle tissue. The clinician also can assess the duration of activity of the toxin preparation. Furthermore, the contralateral eye may serve as a control in each animal preparation, in lower activity injection or to monitor diffusion of toxin activity after higher activity point injections.

Practice of the invention permits manufacture of novel dosage forms which are safer to administer, and permits expansion of chemodenervation therapies to the management of disease states in larger muscles and muscle groups while reducing the risk of side effects. Thus, in another aspect, the invention comprises a novel article of manufacture comprising a package containing a neurotoxin-derived pharmaceutical for chemically inducing in vivo, upon injection of a unit dose of the pharmaceutical into a point in a muscle, at least partial denervation in a predetermined volume of muscle tissue spaced about the injection point. Printed on the label for the package or as an insert is information indicative of the volume of in vivo activity of a unit dose of the pharmaceutical. The physician thus can purchase, for example, a pharmaceutical preparation known in advance to induce partial chemodenervation within, for example, 3 mm, 10 mm, or 30 mm about the site of injection.

With knowledge of the gross or microscopic anatomy of the muscle or muscle group involved, the physician can chemically denervate reproducibly a preselected volume of muscle tissue without inducing significant paresis in muscle tissue outside the preselected volume. This may be accomplished by selecting a particular unit dosage form and injecting a unit dose in one or more, typically in a number, of spaced apart locations within the muscle to induce denervation within the preselected volume. The physician therefore can more clearly estimate the depth and area of toxin spread.

The exact form of the dose of a pharmaceutical standardized in accordance with the invention can vary. Thus, the pharmaceutical may be lyophilized and in condition to be reconstituted before use, or may comprise a stabilized protein solution. While the invention is unlimited with respect to the nature of the neurotoxin which is standardized, it preferably is practiced on biologicals produced by prokaryotes such as those from the genus Clostridium. The currently most preferred neurotoxin is a botulinum toxin-derived pharmaceutical, most preferably a preparation derived from botulinum toxin type A. It may however take the form of any of the know types of botulinum toxin (A through G) or various engineered proteins which retain the native form's ability to block acetylcholine release.

Knowledge of the in vivo biodistribution of chemodenervating agents gained by the practice of the invention permits very significant expansion of the use of these materials in the management of human disease. The agents may be used safely either for their direct or indirect effects. One example of their indirect effects involves use of such materials in facial cosmetic applications. The administration of an appropriate does of, for example, botulinum toxin, to attenuate tone of muscles about the eyes and forehead can in many cases remove wrinkles characteristic of aging in skin overlying the muscle while inducing only mild, often acceptable muscle weakness. Such chemodenervating agents also may be used to induce cosmetic improvement in hemifacial paralysis by intentionally inducing partial paralysis in the contralateral side of the face thereby to improve bilateral facial symmetry. The materials may be injected at points spaced asymmetrically about the spine within paraspinal muscles to alter muscular support for the spine in juveniles to prevent or ameliorate the development of scoliosis. Injection of low doses of the agents into muscles activating the jaw can retard tooth wear caused by involuntary or unconscious clenching of the teeth.

Examples of direct effects are the treatment of unwanted involuntary pathologic muscle stimulation, i.e., spasm, rigidity, or hyperstimulation, by direct injection throughout, or in the area of innervation of, the affected muscle or muscles. Thus, diseases involving muscle spasticity in general can be treated, typically without regard for its cause. The drug may be used to alleviate overstimulation, rigidity, or spasticity in muscle or muscle groups caused by stroke, cerebral palsey, multiple sclerosis, unilateral or bilateral parkinsonism, and other diseases characterized by spasmodic or continuous muscle hyperstimulation.

Accordingly, it is an object of the invention to provide a novel method of standardizing chemodenervating neurotoxin-derived pharmaceuticals such as botulinum-derived pharmaceuticals. Another object is to standardize botulinum toxin preparations with respect to their zone of denervation when injected in vivo. Another object is to provide novel dosage forms of such agents. Yet another object is to provide novel therapies for muscle spasticity and/or hyperactivation heretofore untreatable or treatable only imperfectly with systemic drugs or surgery. Another object of the invention is to provide a mechanism for testing duration of action and diffusion potential in neurotoxin-based preparations. Another object of the invention is to provide a tool for evaluating diffusion potential of various preparations of botulinum-based pharmaceuticals, e.g., various immunotypes, purifications and formulations.

BRIEF DESCRIPTION OF THE DRAWINGS

Other objects and features of the invention will be apparent from the description and claims which follow and from the drawing wherein

DETAILED DESCRIPTION

Figure 1:
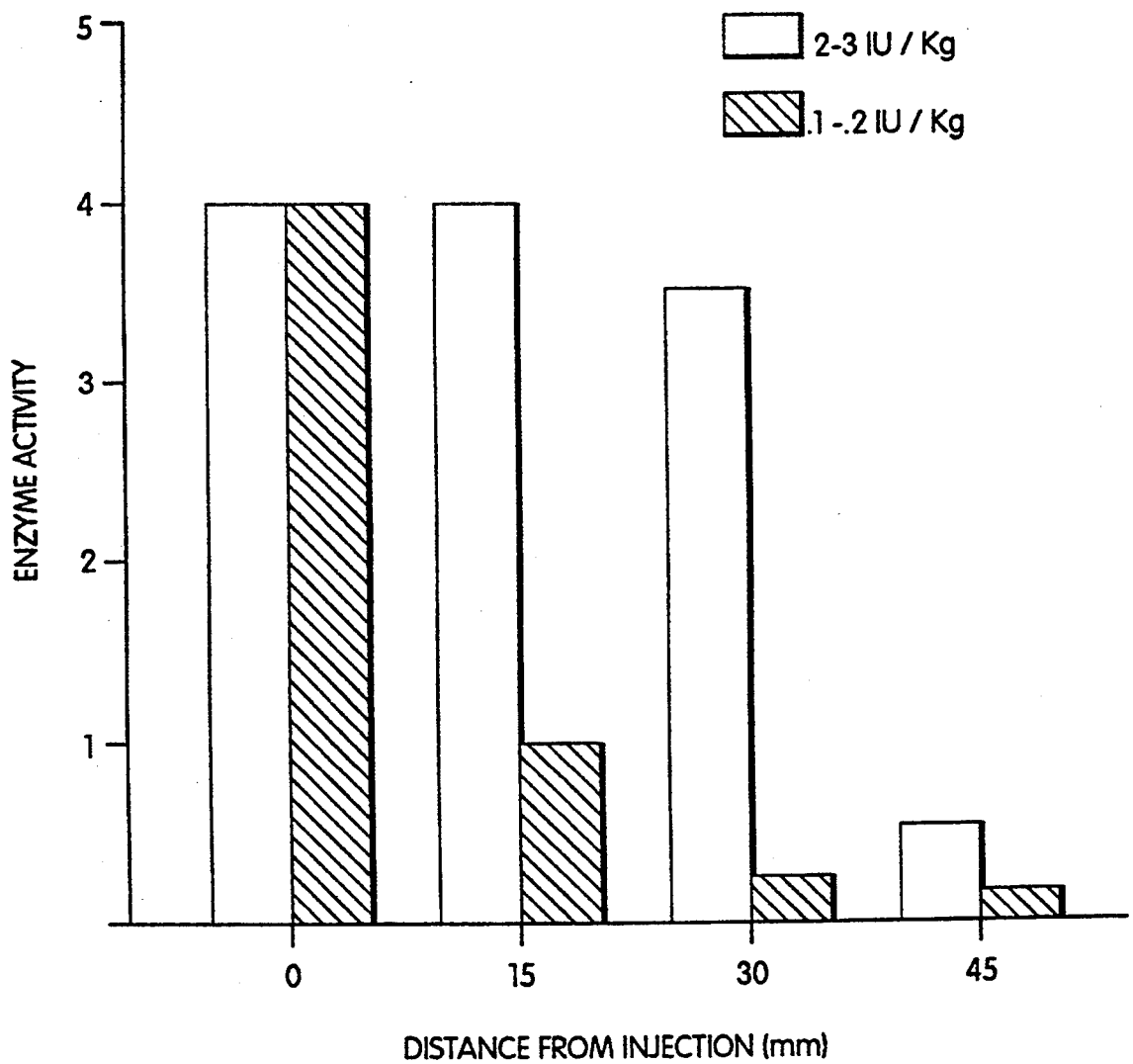
FIG. 1 is a bar graph illustrating measurement of the zone of chemodenervation of two botulinum toxin preparations.

The invention may be practiced using any substance which is capable of interrupting nerve impulse transmission across the neuromuscular junction in a muscle or muscle group. While many such neurotoxins are known, the currently most promising reagents of this type are the family of toxins derived from *Clostridium botulinum*, and the most preferred is pharmaceutical grade botulinum toxin Type A available commercially from Allergan Pharmaceuticals, Inc. under the tradename OCULINUM TM. However, it should be stressed at the outset that it is a fundamental advantage and feature of the invention that it can be applied to any injectable substance which interrupts neuromuscular transmission at the synapse, and that other materials of this type when and if developed to pharmaceutical grade could be used in the novel therapies. Thus, it is contemplated that other materials, protein subunits, recombinantly produced materials, and other various novel types of pharmaceutical preparations can be used in the practice of the invention to advantage. However the work forming the basis of the invention was conducted using both commercially available botulinum toxin-based material identified above, and experimentally synthesized materials. The remainder of the discussion will be limited to these materials, hereinafter referred to simply as "toxin."

Injection of a sublethal dose of a toxin into a muscle or muscle group deposits a bolus of the material intramuscularly which diffuses outwardly to a distance that is a complex and currently unknown function of, inter alia, the identity and amount of diluent if any injected with the toxin, the mass of the toxin, the population of presynaptic receptors about the site of injection, and the current physiological condition of the patient. Diffusion, driven presumably by the concentration gradient, slows as active toxin binds to receptors on the presynaptic membrane. Some portion of the toxin is swept away by the vascular system and distributed systemically. Some other portion may be proteolytically degraded before binding.

Doses far smaller than the $LD_{50}$ for man (believed to be on the order of 2 μg) can paralyze completely, or partially or lightly denervate a muscle volume, depending on dose. The therapeutic effects are achieved at dosage levels in the range between a few I.U. to 500 to 1000 I.U., preferably no more than 500 I.U., and most preferably no more than 300 I.U., administered as a plurality of injections about a muscle or muscle group. Injection of a therapeutic dose results in destruction of a subset of the neuromuscular junctions innervating the muscle but leaves others in a functioning state.

It has been hypothesized that a threshold quantity of the toxin must bind to a particular axon before that axon becomes irreversibly poisoned and the denervation-renervation cycle is initiated. Motor end plates which receive a dose below the threshold presumably recover and participate together with unaffected axons in continued innervation of the muscle. Support for this model of drug action is based on observations that: transient low level retardation of muscle stimulation can be detected in some cases in muscles remote from the site of injection; an animal poisoned intraperitoneally with the toxin upon autopsy shows no histological signs of denervation; and, there is a gradient of denervation about the site of injection. Another factor affecting dose response is the existence of innervation zones within muscles, i.e., there are differences in the microanatomical distribution of neuromuscular junctions within muscles. A literature search suggests that little is known about muscle innervation patterns. However, it is clear that some muscles are enervated more or less uniformly throughout their mass whereas others have a zone of innervation in one region. Thus, particularly in large muscles, the locus of injection within the muscle can influence the physiological response.

The extent of denervation of a muscle can be determined postmortem by sectioning the muscle and staining for acetylcholinesterase activity using the method of Karnovsky (See, Woolf and Coers, *The Innervation of Muscle*, Charles Thomas Pub, Springfield, Ill., 1959). As disclosed below, excision of human muscle previously treated with the toxin, and postmortem sectioning of rabbit muscle about a site of toxin injection, exhibit a gradient of denervation akin to that disclosed by Duchen in mice (See, *J. Neurol. Neurosurg. Psychiat.*, (1970); 33:40–54; *J. Physiol.* (Lond), (1969); 204:17–18P).

In accordance with the invention, the extent of spread of a given dose of a chemodenervating agent is used as a measure of the activity of the preparation, and is used to quantify an appropriate dose for injection into a muscle or muscle group. This permits the physician to confine the action of the toxin to a predetermined volume of muscle and to prevent or minimize the spread of the toxin into adjacent muscle tissue.

The extent of muscular denervation induced by the dose injected can be determined in several ways, one of which is determining the amount of acetylcholinesterase activity. In this embodiment, a given dose of a toxin preparation is injected into the muscle of an experimental animal. After a period of time, typically three to five weeks, which is required to fully establish the denervation field, the animal is sacrificed, and in order to assess toxin spread of the injected dose, sections are taken about the site of injection, for example, 3, 10, 15, 30, 45, and 60 mm from the site. Each of the sections is stained to determine acetylcholinesterase activity. This permits visualization of the zone or field of effective denervation, which can be determined precisely. Alternatively, the muscle may be sectioned through the point of injection across the denervation field and stained so that the gradient can be observed readily. Correlation of these data between, for example, small rodents and simians by direct observation, or between the experimental animals and surgically excised human muscle, backed by clinical experience, provide precise information on the extent of denervation a given quantity of toxin will induce when injected at a given site in a human muscle or muscle group.

Determination of the extent and zone of inhibition of acetylcholine release can be measured by various techniques known to those skilled in the art in addition to acetylcholinesterase staining, including single fiber electromyography (See, for example, Sanders et al., "Botulinum Toxin for Blepharospasm, Single Fiber EMG Studies," *Neurology,* (1985) 35:271–272). The presence of acetylcholinesterase also can be detected by using labeled binding proteins such as polyclonal or monoclonal antibodies labeled with, for example, fluorescein of other fluorescent moiety, colloidal metallic particles, radionuclides or other remotely detectable substance. Antibodies can be produced, using known techniques, to acetylcholine receptors or to acetylcholinesterase, both of which can serve as a marker for effective denervation, or to epitopes which are newly exposed, or which remain after binding of the toxin to the receptor on the presynaptic motor end plate. Other stains may be used such as hematoxylin, eosin, and masson trichrome. Any of these techniques and others that can be devised may be used to determine the extent of diffusion and effective denervation of a given dose of a chemodenervating agent within the muscle of an experimental animal.

Another technique for determining the extent of denervation induced by injecting a chemodenervating preparation into a muscle is determining the decrease in muscle fiber thickness (fiber atrophy) using fiber diameter variation analysis which occurs about the locus after injection of the chemodenervating agent. The change in muscle fiber diameter can be correlated directly to the dose of toxin and to acetylcholinesterase activity. In this method, the desired dosage of toxin is injected into the muscle or muscle group, and allowed to spread to form a denervated area within the muscle or muscle group. Once the denervation field has been established (after about two to five weeks), muscle biopsies are taken at various distances from the injection point and the average muscle fiber diameter at each distance is determined. The diameter of the muscle fibers can be measured by various techniques well known in the art. Preferably a computer-aided system is used which can measure the diameter of muscle fibers obtained from a biopsy, and calculate an average fiber diameter and variation for the sample. For example, a system which is commercially available and can be used for this purpose is the Bioquant II System. Denervation of an area of muscle blocks the release of acetylcholine in the muscle resulting in decreased contractility and fiber atrophy. The decrease in muscle fiber diameter can be correlated with the degree of denervation, thus the area denervated by a given dose of toxin can be accurately determined. A specific example demonstrating this technique is set out in detail in Example 2.

Another embodiment of the present invention permits a very rapid approximation of the denervating effect of a chemodenervating agent. Using this method, the denervating effect is approximated rapidly (e.g., within about 48 hours) using an animal ptosis model. "Ptosis" refers to the downward displacement of an organ, and refers herein to eyelid drooping. In this method, varying dosages of the chemodenervating agent are injected into the muscles or muscle groups which control eyelid movement. In one embodiment, a known quantity of a chemodenervating preparation is injected into the midface of the animals, specifically into the levator palpebral superioris muscle, thereby inducing ptosis in the eyelids of the animals. The degree of ptosis is indicative of the degree of diffusion into the orbit resulting in decreased levator muscle tone and contractility, and thus the extent of denervation induced by the dose injected. For example, in one experiment, severe ptosis was induced in a rabbit injected with 10 IU of a botulinum toxin preparation; severe to moderate ptosis was induced in another rabbit from an injection of 5 IU; and injections of 1.25 and 0.1 IU had no discernable effect. These results enable a manufacturer of the drug to quickly determine an estimate of the potency of a given volume or mass of a particular batch of chemodenervating agent by injecting it into a muscle in the vicinity of the eyes of an animal and observing the resulting ptosis. In addition to ptosis, globe prolapse can be observed as another orbital change resulting from diffusion of toxin into the orbital musculature. The term "globe" as used herein refers to the globe of the eye (bulbus oculi). This method has the advantage that the animal need not be sacrificed, and the results can be evaluated within a relatively short time, e.g., about 48 hours. Duration of action studies, however, may require about one month for complete evaluation.

Use of the technique enables chemodenervating agents to be prepared in various dosage forms and provides nomograms which enable the physician to inject the agents for therapeutic purposes in humans responsibly while eliminating or minimizing side effects caused by unwanted toxin spread beyond the intended denervation zone. Some degree of paresis and muscle weakening beyond the intended locus of denervating action may nevertheless occur. However, the physician may use the techniques and chemodenervating pharmaceuticals standardized as herein disclosed to tailor doses to the selected point or points of injection based on his diagnosis determining the affected muscles, and to predict the duration of activity of new formulaions in clinical studies. The denervating effect therefore can be confined essentially to a given muscle or muscle group despite the observation that the botulinum toxin can spread beyond intervening facial planes and bony structures. Data obtained using the process of the invention to date indicate clearly that the size of the field of action of therapeutic injections of chemodenervating agents is dose dependent. Furthermore, several of the observed complications in established clinical protocols have been correlated to spread of the toxin beyond the intended field of action by retrospective and prospective study of the anatomic injection sites and doses.

FIG. 1 is a graph disclosing data representative of the type that can be generating using the process of the invention. Longissimus dorsi muscle of groups of six New Zealand white rabbits were studied to assess differences in acetylcholinesterase staining activity at varying distances from the site in injection of two separate does of botulinum toxin. The first dose contained four to six I.U. as determined by dilution from a 100 I.U. vial of the commercial preparation; the second contained 0.2 to 0.4 I.U. The toxin was reconstituted at 1.25 I.U. per 0.1 ml physiological saline. The point of injection was marked with a tattoo. The injections were made 5 to 8 mm deep directly into the muscle. A control animal was injected with the saline diluent. After five weeks, the animals were sacrificed, and sections of the muscle were taken 15, 30, and 45 mm caudel from the sites of injections transverse to the spine and in a direction parallel to the spine on a contralateral side. Acetylcholinesterase slide staining was conducted by placing muscle specimens in Baker's solution (10% formol-calcium), which then were refrigerated, and after 24 hours, placed in 0.88 gum sucrose for 2 to 3 hours. The muscle then was sectioned into 20 micrometer sections in a cryostat at a $-20°$ C. and placed on gelatin-coated slides. Acetylcholinesterase activity was demonstrated by Karnovsky's method, and the slides were incubated for 90 minutes at 37° C., washed in distilled water, counterstained with fast green, dehydrated rapidly, and mounted.

At the site of injection, diffuse acetylcholinesterase staining was seen over essentially all muscle fibers. For the larger dose, (2 to 3 I.U./kg) the muscle histology was essentially identical to 15 mm. At 30 mms, a decrease in acetylcholinesterase enzymatic activity was indicated by a reduction in color intensity, but very significant muscle denervation was still apparent. At 45 mm, a very significant reduction in enzyme activity was noted. For the small dose (0.1 to 0.2 I.U./kg) immediately about the site of injection enzyme activity was similar to the larger dose. However, at 15 mm from the site of injection, denervation was markedly diminished, and at 30 mm and 45 mm, enzyme activity was barely above levels observed in control specimens. Contralateral longissimus dorsi biopsy specimens revealed staining intensities similar to those observed in the specimens discussed above, illustrating that toxin diffuses unhindered through facial plans and about bone.

These results demonstrate the feasibility of the standardization process of the invention. That such result can be used to improve the clinical efficacy of botulinum preparations was demonstrated in the clinic as shown in the following examples.

EXAMPLES

Example 1

Retrospective reviews were conducted from the records of patients with adult onset idiopathic spasmotic torticollis who have been given botulinum A toxin for a period of two to thirty-eight months (average 1.1 years) and who had experienced the complications of dysphagia (difficulty in swallowing caused by paresis). In these patients, the toxin had been reconstituted in normal saline ($\approx 100$ I.U./ml) without preservative and injected with a 25 or 27 gauge needle. Patients had been evaluated bi-weekly or immediately for evidence of dysphagia. A single treatment consisted of one or more injections to the sternomastoid muscle or to the posterior cervical muscles or both. The muscles injected had been determined to be dystonic based on palpation, hypertrophy, involuntary spasms, and posture deformity. Each of the 49 injections to the cervical musculature of 26 patients was characterized with respect to dose and injection site. The injections that did not result in dysphagia were then compared with those that did. The data from this retrospective analysis indicated a potential cause-effect relationship between the dysphagia and sternomastoid dosage. Analysis of the data indicated that each patient who experienced dysphagia noted the onset of symptoms within 20 days of the injection and reported a duration of from six days to four weeks. There was no significant difference between total dosage given patients who experienced dysphagia and those who did not. However, if the dose given to individual muscles was evaluated, a significant difference in the dose administered to the sternomastoid muscle was apparent. More specifically, every patient who had experienced dysphagia had had 150 I.U. to 175 I.U.

injected into the sternomastoid muscle. In addition to numeric analysis of dose, every patient who experienced dysphagia had been injected in their sternomastoid muscle, and the complication did not occur if the posterior cervical muscle group was alone injected.

Thereafter, 24 patients were enrolled for a prospective study and were asked to report to the investigator promptly should dysphagia occur. Each patient was contacted within four weeks of injection and specifically questioned to assess whether post-injection dysphagia had occurred. Each of these patients were given a dose of not greater than 100 I.U. in the sternomastoid muscle at three, four, or five injection points, typically five, of 20 to 35 I.U. per injection site. In addition, eight additional injections were given to six patients who initially experienced dysphagia yet benefited substantially from the previous treatment. Patients from this group were injected after a period of at lest five months from the previous injection with a sternomastoid dose of 100 I.U., again 3 to 5 points along the length of the muscle. None of the next 31 injections in the 24 patients were followed by dysphagia. Furthermore, the six patients previously experiencing dysphagia who received eight injections under the new treatment protocol showed no reoccurrence of dysphagia after 20 weeks follow-up.

These data indicate that injection of 100 to 175 I.U. (2–3 I.U./kg) into the sternomastoid can result in diffusion of the botulinum preparation into deeper muscles of the throat resulting in dysphagia manifest by difficulties in speaking, swallowing, or breathing. In contrast, smaller doses of 20 to 30 I.U. spaced 5–15 mm apart, limiting the total dose to less than about 100 I.U. (<2 I.U./kg) in the sternomastoid resulted in no deep muscle involvement causing dysphagia. In these patients the sternomastoid is about 30 mm from the pharanx.

These data are supported further by the histological observation of strips of obicularis oculi muscle (normally discarded) excised from patients undergoing ptosis surgery who had been treated previously with botulinum A for involuntary blepherospasm, and control specimens of obicularis oculi excised from patients with involutional ptosis who had never been injected with botulinum toxin. The test specimens were obtained four weeks to four months after the last botulinum toxin injection and each was treated to assess denervation as disclosed above. Each toxin treated muscle specimen exhibited extensive spread of acetylcholinesterase activity over the individual muscle fibers. The diffuse patter of staining, which was associated with muscle fiber atrophy, made identification of discrete neuromuscular junctions difficult. In contrast, each of the four control specimens showed discrete areas of staining on the muscle fiber surface corresponding to acetylcholinesterase activity and position of neuromuscular junctions of the muscle fiber. These and other observations from the clinical treatment of blepharospasm indicate that 20 I.U. botulinum toxin (0.2–0.4 I.U./kg) will spread less than about 30 cm in human obicularis oculi.

In accordance with the invention the toxin may be prepared in dosage form in conventional biologic standardizations such as $LD_{50}$ but most importantly in terms of a unit dose of the toxin's spread capability. This involves nomogram preparation as outlined above and labeling the pharmaceutical agent with the information to provide the physician with the capability of placing injection sites at preselected intervals on the muscle selectively to denervate the muscle and to limit toxin spread in contiguous muscles. This permits expansion of use of the preparations into procedures such as those described below.

Inhibition of Tooth Wear

The involuntary grinding of teeth characteristic of true bruxism is caused by involuntary and often unconscious contractions of the masseter, temporalis and pterygoid muscles. The masseter and temporalis usually are targeted as the muscles which will undergo chemodenervation. They are injected so as to limit the penetration of the toxin to the volume and body of the muscles. Diffusion should be limited to a distance of no more than 25 to 35 mms. A unit dose injection is given at the surface of each of these muscles at multiple points percutaneously or permucosally. Of course, appropriate dental evaluation to assess the degree of damage or potential damage to the teeth should be conducted prior to application of the toxin. The treatment is repeated periodically, e.g., at three to five month intervals as needed to inhibit jaw clenching to protect the teeth, and to relieve the pain syndrome, if any.

Cosmetic Wrinkle Reduction

Facial expression lines such as the transverse forehead lines or the nasolabial fold are created by attachments of projections of facial muscles into the dermis. Contraction of facial muscles generally is well know to produce the various characteristic forms of facial expressions such as smiling, grimacing, etc. In addition, exaggeration of facial lines also is associated with the aging process. The general principle of the application of the toxin is to limit the tonic contractile state of facial muscles so as to reduce muscle tone and to improve or change the quality and characteristics of facial expression.

The transverse forehead lines may be reduced in intensity by injecting a quantity of toxin with a diffusion field of approximately 10 to 10 mms in four injection sites at the superior border of the forehead and at a point approximately 15 mms superior to the brow. This is done symmetrically on both sides of the forehead. The glabellar lines (the frowning lines in the mid position of the forehead) may be targeted by treating the glabellar muscles with a toxin quantity producing a field of denervation of 5 to 10 mms. The toxin is injected 15 mms above the brow line in the mid position of the forehead. The nasal labial fold lines can be diminished in their intensity by treating the zygomatic major and minor muscles which emanate from zygomatic arch and extend diagonally to the position of the nasal labial fold. An injection of toxin diffusing a distance of 5 to 10 mms over the superior border f these muscles will diminish this line effectively. Furthermore, the position of the lips can be controlled by injecting the zygomatic major and minor muscles. The protrusion of the upper lip can be reduced and even inverted by injection of these muscles. In addition, the protrusion of the lower lip can be reduced by injecting the mentalis muscle at doses producing a denervation field of 5 to 10 mms at the level of the chin approximately 15 mms inferior to the lower lips at a point of approximately 5 mms from the midline.

Stroke and Cerebro-Spinal Injury

Cerebrovascular injuries (stroke and cerebro-spinal injury) can cause spasticity and contractions as a result of paralysis and spasticity. Although the toxin produces a paralysis, it can be useful in reducing muscle mass and in it can be useful in reducing muscle mass and in helping spasticity. Symptomatic spasticity can result in chronic involuntary movements as well as difficulties with contracted postures or contractions of the limbs. The application of the drug to these spastic states involves knowledge of innervation zones of limb muscles, (See, e.g., Woolf et al, supra). The muscle which is involved in the abnormal posture or abnormal movement can be identified with an electromyographic needle. Such muscles can also be identified as causing the posture deformities based on experience and an understanding of the muscle's contractile states on the limb position and movement capabilities. These muscles are impaled with a needle at a site close to the innervation zone. In certain situations, it may be necessary to stimulate the muscle with a stimulating current through a teflon coated electromyographic needle to insure the correct placement of the injections. The toxin is injected at a dose level appropriate to create a field of denervation encompassing the innervation zone of the muscle or the entire muscle. Multiple injections over long muscles may be necessary to isolate the effect over that muscle.

Cerebral Palsy

Cerebral palsy results from various forms of brain damage related to anoxia or vascular insufficiency, usually at the time of birth. The destruction of the central cortex of the central motor system results in involuntary movement spasticity, abnormal posturing, and unwanted contractures of muscles. Physical therapy and occasionally antispasmodic drugs are used to treat cerebral palsy. In situations where spasticity is involved with pain, deformity, involuntary movements, or limitations in functional capabilities of a patient, use of the toxin may be indicated. Application involves targeting muscle groups vital to the patient's disability such as muscles which produce limb deformities or impairments in the volitional movements or in situations where contracture seem to be developing into abnormal postures.

The dosage for treatment of this disease will involve targeting these muscles and using a formulation similar to that used to treat cerebrovascular disease. The prototype for large muscle applications is spasmodic torticollis. The targeted muscle is injected with a dose sufficient to encompass the innervation zone of the muscle.

Multiple Sclerosis

Multiple sclerosis is a disease of white matter of the central nervous system. It involves a demyelination process which leads to impairment of the cortical spinal track and associative tracks in the brain stem. This leads to spinal damage and resultant spasticity. Spasticity in multiple sclerosis can be debilitating because of involuntary movement, contracture, posture deformities, and in certain situations, pain. Use of the toxin is directed and targeted at indications which relieve these particular afflictions relative to the management of the disease.

Again, the toxin is targeted as muscles determined by the physician, neurologist, podiatrist or orthopedic surgeon that appear to be hyperactive. The muscles are injected with a quantity sufficient to encompass volumetrically the muscle or its innervation zone, or both. A working knowledge of muscle anatomy, innervation, and functional anatomy will be needed by the practitioner to achieve optimum results.

Parkinson's Disease

Parkinson's disease is characterized by three basic defects: akinesia (lack of movement); tremor (involuntary movement); and rigidity (increase muscle tone in muscle groups. The toxin can be used to improve the degree of tremor and rigidity present in Parkinsons disease although it probably will be contraindicated in akinesia.

In certain situations in Parkinson's disease, severe dystonias develop in the patients limbs. In these situations, the involuntary movements are exaggerated, spastic, and often painful. Toxin is injected into the muscle in a dose sufficient to encompass the volume of the muscle or its innervation zone or both. It is done with a stimulating electrode needle to an EMG machine or in conjunction with EMG machine to insure the correct placement of the needle in the muscle. The toxin is given in multiple injection pints for large muscles in order to insure an adequate percentage of the innervation zone is encompassed in the injection formulation. The toxin injections must be repeated every three to six months to sustain the desired clinical effect. Total does administered to initiate a given cycle of denervation—reinnervation should in all cases be far below the $LD_{50}$ for the patient.

Example 2

This example demonstrates the correlation between the change in muscle fiber diameter and activity of a botulinum toxin preparation.

METHODS AND MATERIALS:

Longissimus dorsi in 2 to 3 kg brown albino rabbits were injected at a point along the mid-dorsal spine. A tattoo over the skin and muscle was applied at the injection point using India ink. In addition to the tattoo, the injection point was placed anatomically at the dorsal angle of the right scapulae to insure reproducible localization of the injection site even if the tattoo faded or tissue plane sliding made identification of the injection point difficult.

Botulinum A toxin was obtained from Allergan Pharmaceuticals, Inc. in lyophilized form. It was reconstituted in sodium chloride 0.9% for injection and was diluted to 1 IU per 0.1 ml, 2.5 IU per 0.1 ml, 5 IU per 0.1 ml in 10 IU per 0.1 ml. These dilutions were chosen because these concentration are often used in clinical practice. Control injections were made with 0.9% sodium chloride diluent.

After injection, five weeks was allowed to elapse in order to obtain an adequate interval for muscle fiber atrophy and reactivity of acetylcholinesterase staining. The animals then were sacrificed using a lethal injection of Nembutol. (This study was done under the approval of the Animal Studies Protocol, Massachusetts Eye and Ear Infirmary). Dissection was taken down over the dorsal spine removing the latissimus dorsi muscle and exposing the longissimus dorsi muscle down its entire length to the caudal end of the lumbar spine. At this point a ruler was placed over the injection site and 45 mm from the injection site was measured. Biopsies were taken at 15 mm intervals and processed with liquid nitrogen freezing.

Routine hematoxylin and eosin staining was used to analyze fiber size and fiber size variability. This was done in each specimen beginning at the injection site, and at 15 mm intervals to 45 mm from the injection point. Additionally, acetylcholinesterase staining was done by the method of Karnovsky, ibid.

Fiber size averaging and fiber variabilities were done with the Bioquant II computer assisted system. Fiber size variability comparisons were done using a standard statistical F-ratio. Mean fiber diameter for each dose injection was calculated using mean fiber diameters taken from four biopsies over 45 mm length of the muscle at 15 mm intervals and averaging.

Intensity of acetylcholinesterase staining was estimated using reference photographs representing gradations of spread and intensity of staining. These gradations were rated 0–4. The observer matched the acetylcholinesterase staining characteristic of each biopsy taken along the muscle strip with one of the reference photographs depicting the four varying degrees of enzymatic staining intensity and expansion. Each biopsy was matched to the closest gradation on this scale.

RESULTS:

The mean fiber diameter appeared to correlate to the dose of botulinum toxin administered. The mean diameter was determined from summation of counts on four biopsies taken at 15 mm intervals over a linear distance of 4.5 cm from the injection site. The mean muscle fiber diameter after a 10 IU injection was 26.7 microns (s=14.8)(n=1600); mean diameter at 5 IU was 31.7 microns (s=14.6)(n=1600); the mean diameter at 2.5 IU was 30.4 microns (s=14.0)(n=1600); the mean diameter at 1 IU was 30.7 microns (s=11.1)(n=2400). Control fiber diameter was 35.4 microns (s=9.2)(n−160).

Fiber size variability also appeared to correlate directly with the dose administered. Fiber size variability compared against dose is illustrated in Table 1. Variability refers to the change in muscle fiber diameter which resulted from the dose.

TABLE 1

DIFFUSION GRADIENT BASED ON FIBER SIZE VARIATION FROM POINT INJECTION OF BOTULINUM A TOXIN
MEAN VARIANCE OF FIBER SIZE

|         | CONTROL | 10 IU  | 5 IU  | 2.5 IU | 1 IU   |
|---------|---------|--------|-------|--------|--------|
| INJ. PT.| 106     | 246    | 165   | 189    | 141    |
| 15 mm   | 102     | 292    | 262   | 223    | 136    |
| 30 mm   | 77      | 153    | 198   | 217    | 121    |
| 45 mm   | 71      | 198    | 223   | 159    | 107    |
|         | N = 2   | N = 2  | N = 2 | N = 2  | N = 3  |
| AVE VAR*| 89      | 222.25 | 212   | 197    | 126.25 |

Figure 2:
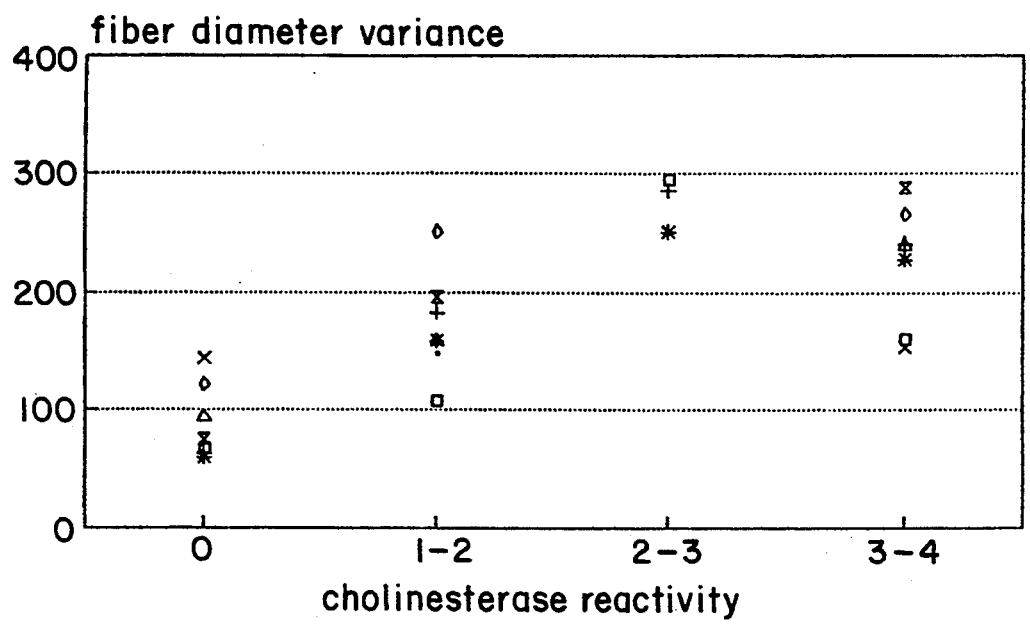
FIG. 2 is a graph illustrating the change in muscle fiber diameter after injection of varying amounts of botulinum toxin.
Figure 3:
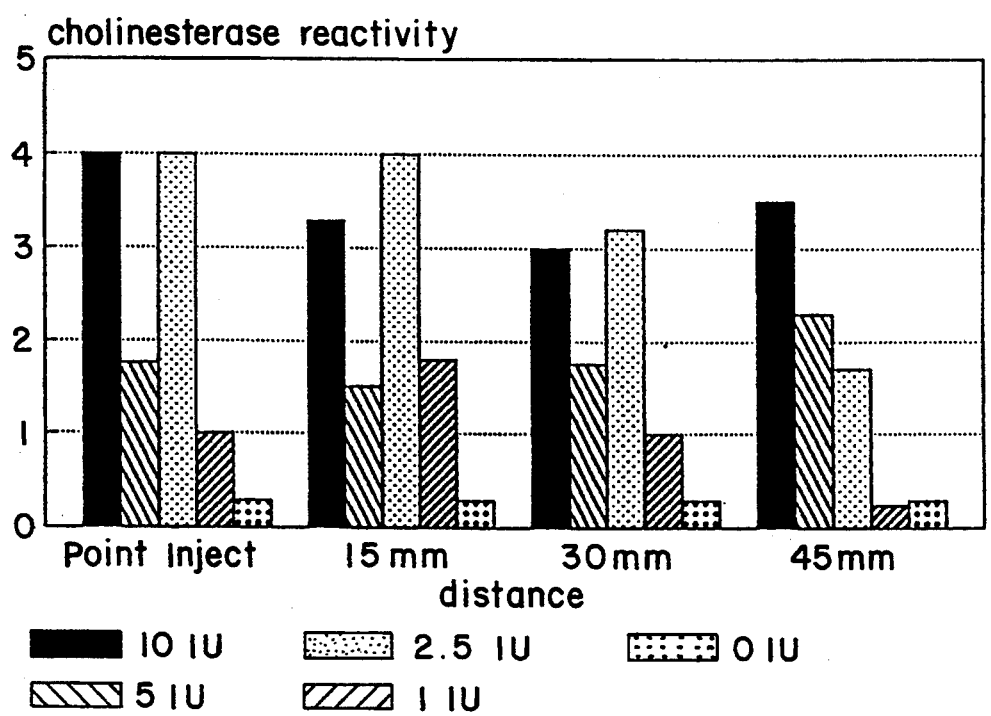
FIG. 3 is a bar graph illustrating the extent of change in muscle fiber thickness in a muscle at various distances from the point of injection for four different dosages of botulinum toxin.

Fiber size variability also correlated with quantification of acetylcholinesterase staining and spread characteristics on muscle fibers, as shown in FIGS. 2 and 3.

The field of biologic activity within the injected muscle was assessed using fiber size variability and acetyl cholinesterase staining characteristics. The diffusion of biologic activity within the injected muscle correlated with the dose administered. Fiber size variability at 1 IU became insignificant compared to controls at 15 microns (F ratio <1.4 based on 200 fiber counts per specimen). At 2.5, 5, 10 IU the biologic effect reflected by fiber size variability was sustained throughout at 45 mm length along the muscle strip. Fiber size variation was significantly different from controls at 11 higher doses down the entire muscle strip (F ratio >1.4). Spread and intensity of acetylcholinesterase staining confirmed the biologic effect diminished at 15 mm for the 1 IU dose. The acetylcholinesterase staining characteristic suggested higher doses (2.5-10 IU) produced a biologic effect through the 45 mm length of the muscle strip.

In order to assess the extramuscular diffusion properties of the botulinum A toxin, fiber diameter variations and fiber diameter size were determined on the contralateral longissimus dorsi muscle at 45 mm from the injection site at each dose. At 10 IU, mean fiber size was 37.3 microns; at 5 IU, 38.4 microns; at 2.5 IU, 37.0 microns and at 1 IU, 34.4 microns. With 10 IU, 2.5 IU and 1 IU and 1 IU the fiber diameter variation was not significantly different from controls and was significantly less than the injection site. As 5 IU, fiber variation approached statistical significant (F=1.55, n=200, p=0.01). Intramuscular fiber diameter variation at 45 mm from injection site was compared to a fiber diameter variation with a muscle biopsy taken 45 mm at an extramuscular location within the contralateral muscle. Fiber size variation was significantly greater in the injected muscle at 45 mm than 45 mm at the extramuscular location for 10 IU (F=2.5, p<0.01), and 5 IU (F=1.7, p<0.01). For 2.5 IU the fiber variation comparing the intramuscular injection and the extramuscular injection was not significant. This data indicated that linear spread of biologic effect was greater within the injected muscle than in a remote muscle at an equivalent distance from the point injection of botulinum toxin. The acetylcholinesterase staining characteristic and the fiber variability pattern confirmed the presence of a dose dependent field of action for botulinum A toxin.

The results obtained in this example indicate that the degree of fiber atrophy, and fiber size variability as well as intensity of acetylcholinesterase staining are directly related to the dose and activity of toxin at the site of injection. Furthermore, the diffusion characteristic away from the point of injection within the longissimus dorsi muscle appears to be directly related to dose administered. Animals given 2.5 to 10 IU showed substantial and relatively homogeneous diffusion of the toxin's biologic effects down a linear distance of 45 mm within this individual large muscle, whereas the animals given 1 IU demonstrated a gradient of biologic effect inversely related to the distance from the point injection. There appeared to be little detectable biologic effect using fiber size variation and acetylcholinesterase staining characteristics between 15-30 mm from the point injection of 1 IU.

Diffusion properties outside the injected muscle were studied in these experiments using the contralateral longissimus dorsi muscle at 45 mm from the injection point. The fiber variation analysis indicated that biologic effects of the toxin did not disseminate this distance on a muscle remote from the injected muscle; however, substantial biologic effects were noted at this distance within the injected muscle.

Containment of biologic activity within a targeted area of the body represents a desirable goal of botulinum toxin injection therapy. This data offers insight into the intensity and diffusion of biologic activity within the injected muscle and at muscles remote from the injection site. Diffusion of biologic activity within the muscle appears to be a function of dose and can be graduated. The denervation field can be defined as a linear distance from the point injection over which botulinum toxin causes a denervation effect. The degree of denervation as indicated by fiber size atrophy and fiber size variation appears to be a function of dose. The size of the denervation field however is also a function of dose as indicated by the homogeneous effects that larger injection doses produced down the long muscle strip. As denervation field size and degree of fiber atrophy and denervation are dose dependent, larger doses of botulinum toxin can be expected to produce more weakness and fiber atrophy but with greater spread of the toxin from the injection sites. As complications in clinical practice are often related to undesirable toxin spread ("toxin jump"), the field of denervation must be considered in the clinical use of botulinum toxin.

Using cross sectional muscle fiber diameter changes after botulinum injection, it appeared that a fiber atrophy of 25% was possible. Although mean fiber diameter was noted to be substantially smaller in the higher doses of botulinum toxin given, fiber size variability may be a more accurate reflection of muscle tissue denervation response to botulinum toxin injections. Large fiber diameters are very common in recently denervated muscle and the variability is much more pronounced in the presence of these fibers compared to normal muscle tissue. Although the mean fiber diameter has been diminished, the fiber variability appears to be proportionately higher because of presence of large fiber diameters within denervated field in the statistical analysis used in the Example.

The cholinesterase stain generally increases in intensity and spreads over muscle fibers 3 to 4 weeks after botulinum A toxin administration. It is apparent that the intensity of the staining correlates directly with fiber variability.

Since the diffusion of biologic activity away from a point injection is dose related and measurable, it is possible to calculate reasonable diffusion fields away from a site of a given dose of botulinum toxin in clinical protocols. Diffusion fields can be established within injected muscles, within contiguous muscles (muscle groups), and within muscles of various fiber orientations. The clinical significance of this is that the clinician applying botulinum A toxin preferably is knowledgeable of the anatomic distances between important muscles within the area being injected and the action of muscle groups in which the botulinum toxin is administered. Such information can provide a scientific approach to distance determination between injection sites at various doses. Furthermore, the minimum dose necessary to produce a homogeneous denervation effect down a long muscle would be ideal if just that muscle was being targeted for injection. Doses in excess of the minimum dose for homogeneous denervation would be more prone to spread outside the fascial planes of the muscle and into contiguous muscle groups potentially causing complications. The longissimus dorsi diffusion model may also be helpful in studying the biologic activity and diffusion kinetics of various preparations of the toxin.

These results demonstrate that the intensity of biologic effects using acetylcholinesterase mean fiber diameter and fiber size variability appear to relate directly to dose. Furthermore, diffusion away from a point injection of botulinum toxin into a given muscle also is dose related.

Equivalents

The invention may be embodied in other specific forms without departing from the spirit and essential characteristics thereof.

What is claimed is:

1. A method of measuring the denervating activity of a chemodenervating preparation comprising
injecting a quantity of said preparation into a muscle or muscle group of an animal;
permitting said preparation to diffuse within said muscle or muscle group thereby establishing a denervation field; and
determining the extent of the denervation field induced by said quantity of the preparation within said muscle or muscle group.

2. The method of claim 1 wherein the step of determining the extent of the denervation field is performed by measuring inhibition of acetylcholine release about the site of injection.

3. The method of claim 2 comprising determining the local concentration of acetylcholinesterase in regions of said muscle spaced apart from said site of injection.

4. The method of claim 3 wherein the local concentration is determined by histochemical estimation of acetylcholinesterase enzyme activity.

5. The method of claim 1 wherein the step of determining the extent of the denervation field is performed by determining the extent of inhibition of muscle stimulation in regions of said muscle spaced apart from said site of injection by electrophysiologic testing.

6. The method of claim 5 comprising determining the extent of effective muscular stimulation by single fiber electromyography.

7. The method of claim 1 wherein the step of determining the extent of the denervation field is performed by determining the density of acetylcholine receptors or acetylcholinesterase in regions of said muscle spaced apart from said site of injection.

8. The method of claim 7 wherein the density of said acetylcholine receptors or acetylcholinesterase is determined by binding labeled antibodies to said receptors or acetylcholinesterase.

9. The method of claim 1 wherein the step of determining the extent of the dernervation field is performed by measuring the change in muscle fiber diameter.

10. The method of claim 9 wherein the variation in muscle fiber diameter is determined by obtaining a biopsy of the treated muscle or muscle group at various distances from the site of injection and determining the mean muscle fiber diameter and diameter variation thereof.

11. The method of claim 1 wherein the muscle or muscle group comprises an eye muscle or muscle group, and wherein the step of determining the extent of the dernervation field is performed by observing the degree of ptosis or globe prolapse resulting from said injection.

12. The method of claim 1 wherein said preparation is a botulinum toxin-derived preparation.

13. A method of rapidly determining the extent of denervation induced by a unit quantity of a chemodenervating preparation comprising the steps of:
injecting said unit quantity of said chemodenervating preparation into a muscle or muscle group which controls eyelid movement of an animal; and
ascertaining the degree of ptosis or globe prolapse resulting from said injection, wherein said degree of ptosis or globe prolapse is indicative of the spatial extent of denervation induced by said unit quantity.

14. The method of claim 13 wherein the preparation is injected into the levator palpebral superioris muscle.

15. The method of claim 13 wherein said chemodenervating preparation comprises a botulinum toxin preparation.

16. The method of claim 13 wherein said ascertaining step further comprises determining the diffusion capability of said chemodenervating preparation.

* * * * *

UNITED STATES PATENT AND TRADEMARK OFFICE
CERTIFICATE OF CORRECTION

PATENT NO. : 5,401,243
DATED : March 28, 1995
INVENTOR(S) : Gary E. Borodic

It is certified that error appears in the above-identified patent and that said Letters Patent is hereby corrected as shown below:

<u>Title page,</u>
Item [63], should read as follows:
-- [63] Continuation-in-part of Ser. No. 08/004,090, Jan. 13, 1993, Pat. No. 5,298,019, which is a continuation of Ser. No. 07/570,395, Aug. 21, 1990, Pat. No. 5,183,462. --

Signed and Sealed this

Thirteenth Day of July, 2004

JON W. DUDAS
*Acting Director of the United States Patent and Trademark Office*